United States Patent
Toyoshima et al.

[11] Patent Number: 5,891,118
[45] Date of Patent: Apr. 6, 1999

[54] ABSORBENT ARTICLE

[75] Inventors: Yasuo Toyoshima; Tetsuya Kusagawa; Mitsugu Hamajima; Minoru Nakanishi; Yuji Yana; Akihiko Saka, all of Tochigi-ken, Japan

[73] Assignee: Kao Corporation, Tokyo, Japan

[21] Appl. No.: 705,049

[22] Filed: Aug. 29, 1996

[30] Foreign Application Priority Data

Sep. 5, 1995 [JP] Japan ................................... 7-228386
Oct. 17, 1995 [JP] Japan ................................... 7-268781

[51] Int. Cl.$^6$ .................................................. A61F 13/15
[52] U.S. Cl. ........................ 604/366; 604/380; 604/382; 604/387; 604/385.1
[58] Field of Search ................................. 604/365–366, 604/378–383, 385.1, 386, 387

[56] References Cited

U.S. PATENT DOCUMENTS

| | | | |
|---|---|---|---|
| 3,575,174 | 4/1971 | Mogor | 604/385.1 |
| 4,059,114 | 11/1977 | Richards . | |
| 4,518,451 | 5/1985 | Luceri et al. | 604/378 |
| 4,781,710 | 11/1988 | Megison et al. . | |
| 4,790,838 | 12/1988 | Pigneul et al. | 604/366 |
| 5,312,386 | 5/1994 | Correa et al. . | |

FOREIGN PATENT DOCUMENTS

| | | |
|---|---|---|
| 57-45178 | 9/1982 | Japan . |
| 64-45801 | 2/1989 | Japan . |
| 288625 | 7/1990 | Japan . |
| 2277453 | 11/1990 | Japan . |
| 333622 | 4/1996 | Japan . |

*Primary Examiner*—John G. Weiss
*Assistant Examiner*—K. M. Reichle
*Attorney, Agent, or Firm*—Birch, Stewart, Kolasch & Birch, LLP

[57] ABSTRACT

A substantially elongated absorbent article having a liquid permeable topsheet, a liquid impermeable backsheet, an absorbent member interposed between the topsheet and the backsheet, and a pair of hydrophobic areas along opposing longitudinal side portions of an upper surface of the absorbent article inwardly from longitudinal side edges of the absorbent article, the hydrophobic areas each having a continuous or discontinuous antileakage groove formed along a respective one of the longitudinal side portions, wherein a width of each of the antileakage grooves is from 0.1 mm to 20 mm, a ratio of a depth of each of the antileakage grooves with respect to a thickness of a portion of the absorbent article where no antileakage groove is formed is from 0.01 to 0.8, and the depth of each of the antileakage grooves is from 0.1 mm to 12 mm.

16 Claims, 6 Drawing Sheets

ABSORBENT ARTICLE

BACKGROUND OF THE INVENTION

1. Field of the Invention

This invention relates to an absorbent article such as a sanitary napkin or an incontinent pad, and more particularly to an absorbent article which exhibits excellent antileakage properties and also provides excellent feeling during use.

2. Description of Related Art

Heretofore, an absorbent article such as a sanitary napkin had problems such as (a) discharged body fluids flow on the surface of a topsheet without being absorbed by an absorbent member, (b) discharged body fluids ooze sideways in the absorbent article in the topsheet, and (c) body fluids once absorbed exude to the topsheet of the absorbent article and ooze sideways, thereby leaking from the side portions.

Thus, in order to overcome the above problems, (1) Japanese Patent Application Laid-Open 64-45801 and Japanese Patent Publication 57-45178 and (2) Japanese Utility Model Application Laid-Open 2-88625, etc. propose an absorbent article comprising a groove disposed in the longitudinal direction of the absorbent article, whereas (3) Japanese Utility Model Application Laid-Open 3-33622 and Japanese Patent Application Laid-Open 2-277453, etc. propose another absorbent article comprising antileakage walls on side edge portions of the absorbent article.

However, the absorbent articles according to (1), (2) and (3) above do not yet fully overcome the above problems.

In the absorbent articles according to the proposals provided in (1), (2) and (3) above, as long as the absorbent article is worn in an ideal state such that both the grooves and antileakage walls are maintained in the same stable configuration as before being worn, occurrence of side leakage of body fluids can be prevented to some extent by trapping the surface-flowing body fluids by the grooves and antileakage walls. However, with these absorbent articles the distance between the topsheet and the absorbent member must be small, and as a consequence the body fluids once absorbed are readily returned to the topsheet from the absorbent member. The result is that the body fluids which return to the topsheet unfavorably ooze out of the topsheet and leak therefrom.

SUMMARY OF THE INVENTION

It is an object of the present invention to provide an absorbent article, in which the surface-flow of liquid and oozing of liquid in the topsheet, which cause side leakage, are suppressed and side leakage preventing properties thereof are remarkably improved.

As a result of extensive search and development for solutions to the above problems, it has been found that the above object can be achieved by an absorbent article which has an antileakage sheet such as the backsheet or the like disposed along opposing longitudinal side portions of an upper surface thereof, a pair of hydrophobic areas formed thereon, and grooves formed respectively in the hydrophobic areas in the longitudinal direction of the absorbent article.

The present invention has been accomplished on the basis of the above finding. The present invention provides a substantially elongated absorbent article having a liquid permeable topsheet, a liquid impermeable backsheet, and an absorbent member interposed between said topsheet and said backsheet, said absorbent article further comprising:

a pair of hydrophobic areas along opposing longitudinal side portions of an upper surface of the absorbent article inwardly from longitudinal side edges of said absorbent article, said hydrophobic areas each having a continuous or discontinuous antileakage groove formed along a respective one of the longitudinal side portions wherein a width of each of said antileakage grooves is from 0.1 mm to 20 mm, a ratio of a depth of each of said antileakage grooves with respect to a thickness of a portion of said absorbent article where no antileakage groove is formed is from 0.01 to 0.8, and the depth of each of said antileakage grooves is from 0.1 mm to 12 mm.

The present invention also provides an absorbent article wherein the hydrophobic areas are formed by providing antileakage sheets comprising the liquid impermeable backsheet or another antileakage sheet.

The present invention also provides an absorbent article wherein the width of each of the antileakage grooves is from 0.1 mm to 10 mm, the ratio of the depth of each of the antileakage grooves with respect to the thickness of a portion of the absorbent article where no antileakage groove is formed is from 0.3 to 0.8 or from 0.01 to 0.5, and the depth of each of the antileakage grooves is from 1 mm to 8 mm or from 0.1 mm to 8 mm.

The present invention also provides an absorbent article wherein the width of each of the hydrophobic areas is from 3 mm to 30 mm, and the width of the absorption area located between the pair of hydrophobic areas is from 30 mm to 70 mm.

The present invention also provides an absorbent article wherein each of the antileakage grooves has at least one hole portion so that body fluids can be introduced into the absorbent member through the hole portion.

The present invention also provides an absorbent article wherein the depth of each of the antileakage grooves is from 0.3 mm to 8 mm.

The present invention also provides an absorbent article wherein each of the antileakage grooves comprises a bottom portion and a peripheral wall portion, and the hole portion is formed in an area between the bottom portion and the peripheral wall portion.

The present invention is also directed to a method for preparing an absorbent article, which comprises;

feeding a precursor of an absorbent article having a topsheet, a backsheet and an absorbent member and having hydrophobic areas through an emboss roller thereby forming an antileakage groove along the longitudinal direction of the hydrophobic areas.

The absorbent article of the present invention excells in preventing side leakage by suppressing the surface flow of liquid and oozing of liquid in the topsheet which cause side leakage.

DETAILED DESCRIPTION OF THE EMBODIMENT

The present invention will now be described in more detail with reference to the drawings.

First, the first embodiment of a sanitary napkin serving as an absorbent article of the present invention will be described with reference to FIGS. 1 and 2.

Figure 1:
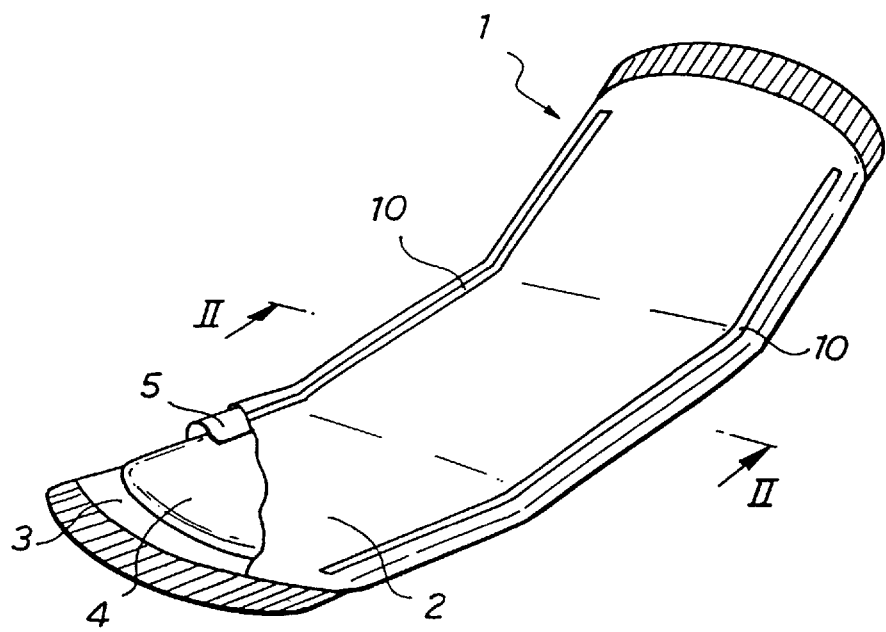
FIG. 1 is a partly cut-away perspective view showing the first embodiment of a sanitary napkin serving as an absorbent article of the present invention.
Figure 2:
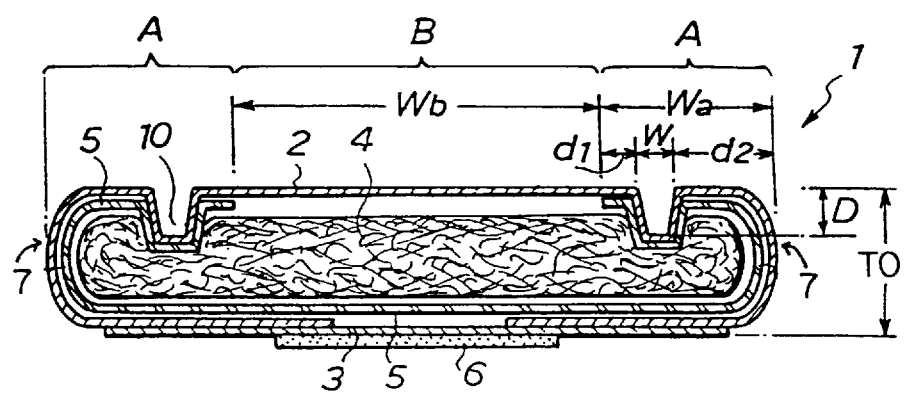
FIG. 2 is a sectional view taken on line II—II of the sanitary napkin of FIG. 1.

Here, FIG. 1 is a partly cut-away perspective view showing the first embodiment of a sanitary napkin as an absorbent article of the present invention, and FIG. 2 is a sectional view taken on line II—II of the sanitary napkin according to FIG. 1.

A sanitary napkin 1 as an absorbent article according to the first embodiment of FIGS. 1 and 2 comprises a liquid permeable topsheet 2, a liquid impermeable backsheet 3, and an absorbent member 4 interposed between the topsheet 2 and the backsheet 3 and has a substantially elongated shape, as per known sanitary napkins.

More specifically, as shown in FIGS. 1 and 2, in the sanitary napkin 1, the topsheet 2 is designed to cover an upper surface, longitudinal side surfaces and a rear surface of the absorbent member 4, and the backsheet 3 is secured through adhesive to the topsheet at a rear surface of the absorbent member 4. An antileakage sheet 5 (an antileakage sheet other than the backsheet) can be further disposed between the absorbent member 4 and the topsheet 2.

Adhesive is applied to a lower surface of the backsheet 3 to form a slipping-off preventing portion 6.

Here, the material for forming the topsheet 2, the backsheet 3 and the absorbent member 4 is not particularly limited and it can be selected from any commonly known material.

Also, as the material for forming the antileakage sheet 5, any sheet having antileakage properties and used for ordinary sanitary napkins can be employed without any limitation.

The sanitary napkin 1 is formed thereon with the antileakage sheet 5 serving as an antileakage sheet at longitudinal side portions of an upper surface thereof (on the side of the topsheet 2) and inwardly toward a liquid absorption area B (as later described) from side edges 7, thereby forming a pair of hydrophobic areas A. Each of the hydrophobic areas A has a continuous antileakage groove 10 formed in the longitudinal direction of the sanitary napkin.

More specifically, the antileakage sheet 5 is disposed between the absorbent member 4 and the topsheet 2, and covers the lower surface, longitudinal side edges, and longitudinal side portions of the upper surface of the absorbent member 4, thereby forming a pair of hydrophobic areas A on the longitudinal side portions of the upper surface of the sanitary napkin and also a liquid absorption area between the hydrophobic areas.

The width w of each antileakage groove 10 is preferably from 0.1 mm to 20 mm, and more preferably from 0.1 mm to 10 mm.

The ratio (D/TO) of the depth D of each antileakage groove with respect to the thickness TO of a portion of the sanitary napkin 1 where no antileakage groove is formed is preferably from 0.01 to 0.8. The depth D of each of the antileakage grooves 10 is preferably from 0.1 mm to 12 mm.

In designing a sanitary napkin exhibiting an enhanced antileakage performance which is worn for a long time, such as a sanitary napkin for overnight use, it is preferred that the antileakage groove 10 is reliably formed. To this end, the width W of each of the antileakage grooves is preferably from 0.1 mm to 10 mm, the ratio (D/TO) of the depth D of each of the antileakage grooves 10 with respect to the thickness TO of a portion of the absorbent article where no antileakage groove is formed is preferably from 0.3 to 0.8, and the depth D of each of the antileakage grooves 10 is preferably from 1 mm to 8 mm.

When enhancing the feeling during use of the sanitary napkin by employing, for example, an absorbent member comprising soft fluff pulp or the like, it is preferred that the antileakage groove is made shallower. To this end, the width W of the antileakage groove 10 is preferably from 0.1 mm to 10 mm, the ratio (D/TO) of the depth D of each of the antileakage grooves 10 with respect to the thickness TO of a portion of the absorbent article where no antileakage groove is formed is preferably from 0.01 to 0.5, and the depth D of each of the antileakage grooves 10 is preferably from 0.1 mm to 8 mm, and particularly preferred from 0.3 mm to 8 mm.

As described above, it is preferred that the ranges of the depth of the antileakage groove 10 and the ratio of the depth of the antileakage groove 10 with respect to the thickness of the absorbent article are selected appropriately depending on the performance required and its use.

If the width w of the antileakage grooves 10 is smaller than 0.1 mm, suppression of the spread of the body fluids which flow on the upper surface of the topsheet or ooze through the interior of the surface material via the antileakage groove 10 is occasionally lessened. In contrast, if the width w of the antileakage groove 10 is more than 20 mm, the feeling during wear is sometimes bad.

If the ratio of the depth D of the antileakage groove 10 with respect to the thickness TO of a portion of the sanitary napkin 1 where no antileakage groove is formed is smaller than 0.01, the antileakage groove 10 is too shallow to always effectively trap the body fluids which flow on the upper surface or ooze through the interior of the surface material. In contrast, if the ratio of the depth D of the antileakage groove 10 with respect to the thickness T0 of a portion of the sanitary napkin 1 where no antileakage groove is formed is larger than 0.8, sometimes the feeling during wear is bad because the portion where the antileakage groove 10 is formed is compressed hard to increase the rigidity of the portion where the antileakage groove 10 is formed.

If the depth D of each antileakage groove 10 is smaller than 0.1 mm, the antileakage groove 10 becomes too shallow to always effectively trap the body fluids which flow on the upper surface or ooze through the interior of the surface material. In contrast, if the depth D of each antileakage groove 10 is larger than 12 mm, the thickness of the entire absorbent article having such designed antileakage groove 10 becomes too large and sometimes the feeling during wear is bad.

The width Wa of each hydrophobic area A is preferably from 3 mm to 30 mm, and the width Wb of the liquid absorption area B located between the pair of hydrophobic areas A is preferably 30 mm to 70 mm. If the width Wa of each hydrophobic area A is smaller than 3 mm, the hydrophobic area becomes too narrow to easily form the antileakage groove 10 therein. In contrast, if the width Wa of each hydrophobic area A is larger than 30 mm, sometimes absorption ability is bad because the width of the absorption area B becomes too narrow. If the width Wb of the absorption area B is smaller than 30 mm, sometimes it becomes difficult to smoothly absorb body fluids under various wearing conditions because the absorbing surface is too narrow. In contrast, if the width Wb of the absorption area B is larger than 70 mm, sometimes the feeling during wear is bad because the width of the entire absorbent article having such designed absorption area B becomes too large.

The distance d1 from an inner side edge of each hydrophobic area A to each antileakage groove 10 is preferably from 1 mm to 20 mm, and the distance d2 from an outer side edge (side edge of the sanitary napkin) of the hydrophobic area A to each antileakage groove 10 is preferably from 1 mm to 20 mm. If the distance d1 is smaller than 1 mm, the amount of body fluids spreading to the groove is increased because the hydrophobic area becomes too narrow. In contrast, if the distance d1 is larger than 20 mm, sometimes the area of the absorption area is reduced because the hydrophobic area from the absorption area B to the antileakage groove B is increased. If the distance d2 is smaller than 1 mm, the distance from each antileakage groove 10 to the side edge of the absorbent article is short, and side leakage may occur because underwear contacts the antileakage groove 10 depending on wearing conditions. If the distance d2 is larger than 20 mm, sometimes the hydrophobic areas formed outwardly of the antileakage grooves 10 cover the grooves during wear of the sanitary napkin.

Since the sanitary napkin 1 according to this embodiment has the antileakage grooves 10 at the hydrophobic areas A, the body fluids once absorbed do not ooze out again onto the surface to cause surface flow, and oozing of the body fluids in the topsheet can be suppressed. Moreover, owing to the provision of the antileakage grooves 10, alone, oozing of the body fluids can be effectively suppressed. Further, even if the napkin is somehow twisted during use of the sanitary napkin, the space and step of each antileakage groove 10 can be maintained and the antileakage properties are not lowered (this effect is particularly significant when the antileakage grooves 10 satisfy the above-mentioned ranges of width and depth).

Since the body fluids do not ooze out at the hydrophobic areas, pooling of liquid in the antileakage grooves which causes an unpleasant feeling for the user does not occur.

Accordingly, the absorbent article according to the present invention excells in preventing leakage and providing a pleasant feeling during use and is sanitary.

The sanitary napkin 1 according to this embodiment can easily be prepared, through a commonly known method, by providing a sanitary napkin having no groove and then compressing (while heating, if necessary) the sanitary napkin in its longitudinal direction by emboss rolling or the like.

Next, the second through fifth embodiments of an absorbent article of the present invention will now be described with reference to FIGS. 3 through 6.

Figure 3:
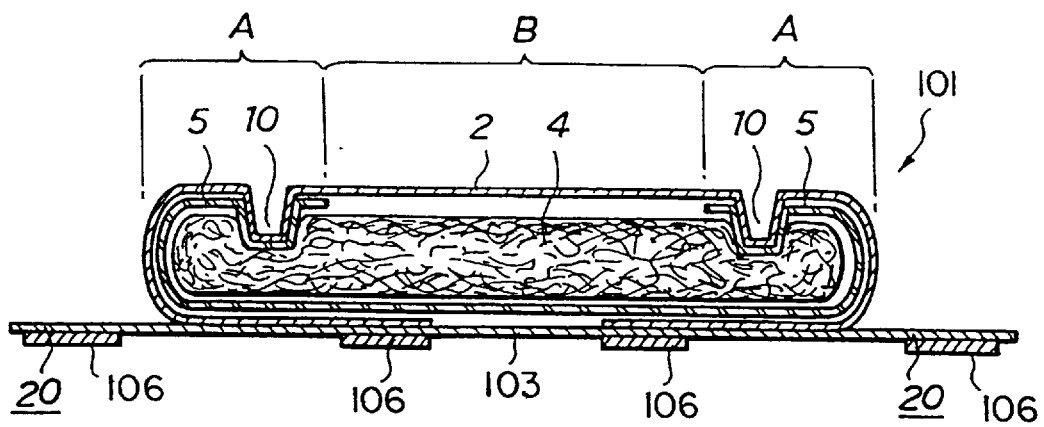
FIG. 3 is a width-wise sectional view (corresponding to FIG. 2) showing the second embodiment of a sanitary napkin serving as the absorbent article of the present invention.
Figure 4:
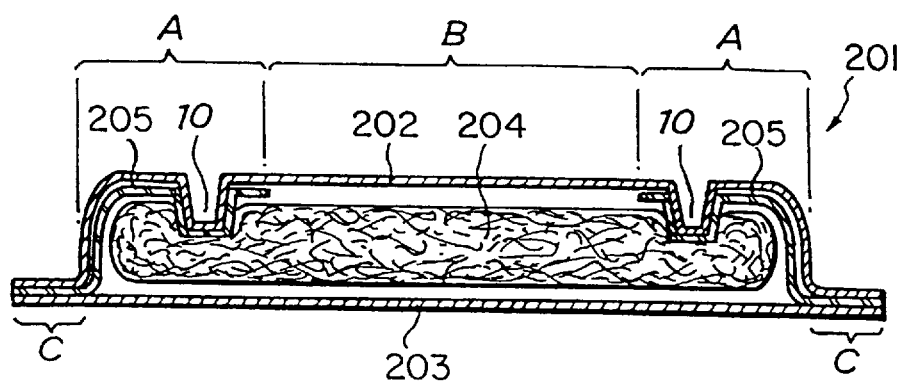
FIG. 4 is a width-wise sectional view (corresponding to FIG. 2) showing the third embodiment of a sanitary napkin serving as the absorbent article of the present invention.
Figure 5:
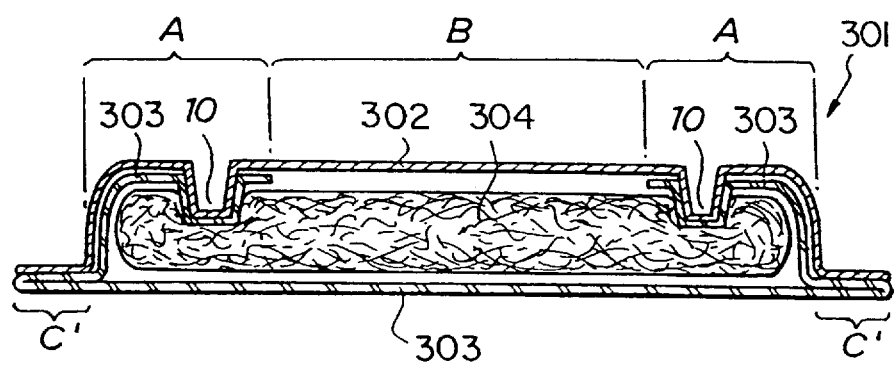
FIG. 5 is a width-wise sectional view (corresponding to FIG. 2) showing the fourth embodiment of a sanitary napkin serving as the absorbent article of the present invention.
Figure 6:
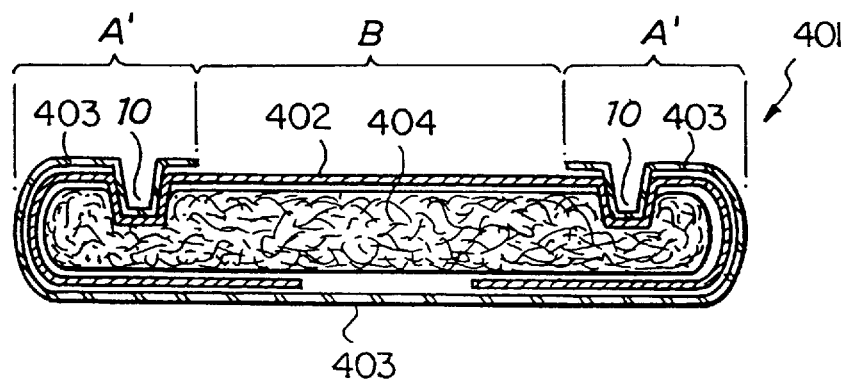
FIG. 6 is a width-wise sectional view (corresponding to FIG. 2) showing the fifth embodiment of a sanitary napkin serving as the absorbent article of the present invention.

Here, FIG. 3 is a width-wise sectional view (corresponding to FIG. 2) showing the second embodiment of a sanitary napkin serving as the absorbent article of the present invention, FIG. 4 is a width-wise sectional view (corresponding to FIG. 2) showing the third embodiment of a sanitary napkin serving as the absorbent article of the present invention, FIG. 5 is a width-wise sectional view (corresponding to FIG. 2) showing the fourth embodiment of a sanitary napkin serving as the absorbent article of the present invention, and FIG. 6 is a width-wise sectional view (corresponding to FIG. 2) showing the fifth embodiment of a sanitary napkin serving as the absorbent article of the present invention.

In the descriptions of the second through fifth embodiments, the features different from those of the sanitary napkin of the first embodiment will be particularly described. For the features which are not particularly referred to, the descriptions made with respect to the sanitary napkin of the first embodiment are applicable, where appropriate. Component members which are identical to those of the first embodiment are denoted by identical reference numerals.

A sanitary napkin 101 according to the second embodiment shown in FIG. 3 has a pair of flaps 20 which are formed by extending the backsheet 103 outwardly from the napkin at the central portion in the opposing longitudinal side portions of the napkin and has a slipping-off preventing portions 106.

In a sanitary napkin 201 according to the third embodiment shown in FIG. 4, the topsheet 202 covers the upper surface and longitudinal side surfaces of the absorbent member 204 and extends outwardly from side edges of the absorbent member 204 at the lower surface of the sanitary napkin 201. The extended portions of the topsheet 202 are adhered to the backsheet 203 respectively through antileakage sheets 205 each of which serves as an antileakage sheet, thereby forming side flap portions C. The antileakage sheets 205 are also disposed at the longitudinal side portions on the upper surface of the sanitary napkin 201 between the absorbent member 204 and the topsheet 202.

In a sanitary napkin 301 according to the fourth embodiment shown in FIG. 5, the backsheet 303 serving as an antileakage sheet extends outwardly from side edges of the absorbent member 304 at a lower surface of the sanitary napkin 301, and is then bent towards the absorbent member 304 to cover the side surfaces and side portions of the upper surface of the absorbent member 304. On the other hand, the topsheet 302 covers the upper surface and the longitudinal side surfaces of the absorbent member 304 and extends outwardly from the side edges of the absorbent member 304 at the lower surface of the sanitary napkin 301. The extended portions of topsheet 302 are adhered to the bent backsheet 303, to thereby form side flap portions C'.

That is, in the sanitary napkin 301 according to the fourth embodiment, the hydrophobic areas A are formed by having the backsheet 303 serving as antileakage sheets disposed on side portions of the upper surface. As discussed, the hydrophobic areas can be formed by the backsheet serving as an antileakage sheet, or by sheets serving as antileakage sheets other than the backsheet as in the above-mentioned first embodiment.

In a sanitary napkin 401 according to the fifth embodiment shown in FIG. 6, the topsheet 402 is in contact with the absorbent member 404. The backsheet 403 which serves as an antileakage sheet covers the upper surface of the topsheet 402 and the lower surface, the longitudinal side surfaces, and the longitudinal side portions of the upper surface of the sanitary napkin 401, to thereby form the hydrophobic areas A'.

In this way, in the hydrophobic area A' either the topsheet or the backsheet (or another antileakage sheet) are located at the outermost upper surface of the absorbent article.

The absorbent article according to the present invention should, by no means, be limited to the first through fifth embodiments but it can be modified in various ways without departing from the spirit and scope of the present invention.

For example, in the first through fifth embodiments, continuous antileakage grooves 10 are provided but the present invention should not be limited to this. The sanitary napkin may be provided with discontinuous antileakage grooves 10 obtained by arranging a plurality of antileakage grooves 10 having various shapes including tetragon shapes, such as a rectangular shape, a circle, etc., in the longitudinal direction of the absorbent article.

Similarly, the configuration (sectional configuration) of each antileakage groove 10 is not limited to the first through fifth embodiments, and various configurations can be adopted. For example, the antileakage groove 10 may have a configuration in which its bottom surface portion exhibits an uneven shape, one in which its cross section exhibits a triangular shape, one in which its bottom surface portion is further depressed downwardly, or the like. Two or more of the antileakage grooves 10 may be provided at each longitudinal side portion.

The sixth and seventh embodiments of an absorbent article according to the present invention will now be described with reference to FIGS. 7 through 9.

Figure 7:
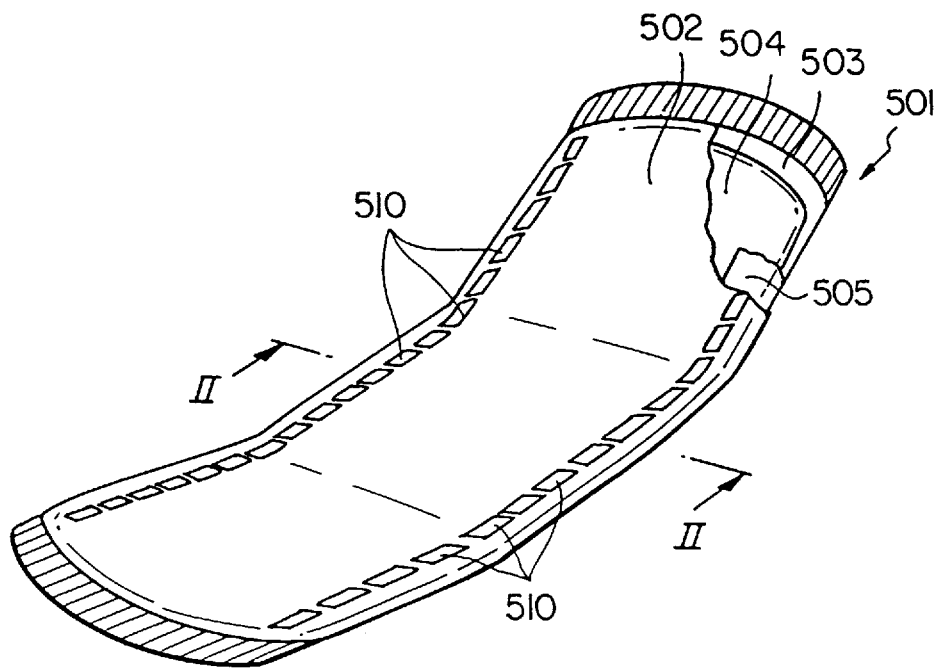
FIG. 7 is a partly cut-away perspective view showing the sixth embodiment of a sanitary napkin serving as an absorbent article of the present invention.

Here, FIG. 7 is a partly cut-away perspective view showing the sixth embodiment of a sanitary napkin serving as the absorbent article of the present invention. FIG. 8 is a sectional view taken on line II—II of the sanitary napkin of FIG. 7. FIG. 9 is a width-wise sectional view showing the seventh embodiment of a sanitary napkin serving as the absorbent article of the present invention.

For the features which are not particularly referred to, the descriptions made with respect to the sanitary napkin of the first embodiment are applicable, where appropriate. Component members which are identical to those of the first embodiment are denoted by identical reference numerals.

In a sanitary napkin 501 according to the sixth embodiment shown in FIG. 7, each of the antileakage grooves 510 has a hole portion 511, so that the body fluids can be introduced through the hole portion 511.

More specifically, in the sanitary napkin 1 according to this embodiment, the antileakage sheet 505 serving as an antileakage sheet covers the lower surface, the longitudinal side edges and the longitudinal side portions of the upper surface of the absorbent member 504 between the absorbent member 504 and the topsheet 502.

Owing to this arrangement, a pair of hydrophobic areas A" are formed on longitudinal side portions of the upper surface of the sanitary napkin, and an absorption area B" is formed between the hydrophobic areas A".

The antileakage grooves 510 are not particularly limited in configurational pattern. In this embodiment, each of the grooves takes the form of a parallelogram of the same type and the longitudinal side edge of each antileakage groove 510 extends in the longitudinal direction of the sanitary napkin 501 and its width-wise side edge is inclined relative to the width direction of the sanitary napkin 501.

The number and pitch arrangement of the antileakage grooves 510 are not particularly limited. However, it is preferred that the grooves 510 are arranged such that there is no area where the antileakage groove 510 is not provided in the longitudinal direction of the sanitary napkin and slanted portions are overlapped with each other.

Figure 8:
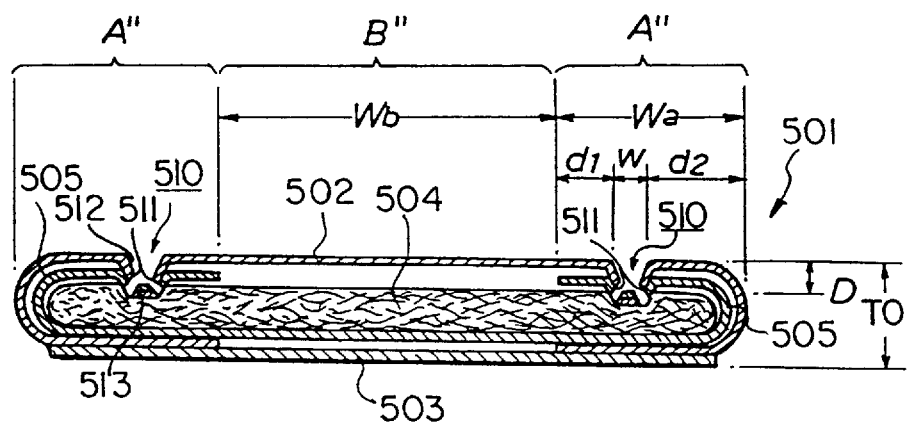
FIG. 8 is a sectional view taken on line II—II of the sanitary napkin of FIG. 7.

In the sixth embodiment, as shown in FIG. 8, each of the antileakage grooves 510 comprises a bottom surface portion 513 and a peripheral wall portion 512. The hole portion 511 is formed in an area of connection between the bottom surface portion 513 and the peripheral wall portion 512. The configuration of the hole portion is not particularly limited. However, the size (dimensional area) of the hole portion is preferably from 0.1 mm$^2$ to 20 mm$^2$, more preferably from 0.2 mm$^2$ to 10 mm$^2$.

If the size is smaller than 0.1 mm$^2$, the ability to absorb the body fluids from the hole portion is degraded. In contrast, if the size is larger than 20 mm$^2$, the body fluids sometimes return from the absorbent member towards the upper surface when pressure is applied thereto.

The width w of each antileakage groove 510 is preferably from 0.1 mm to 20 mm, more preferably from 0.1 mm to 10 mm.

The ratio (D/TO) of the depth D of the antileakage groove 510 with respect to the thickness TO of a portion of the sanitary napkin 501 where no antileakage groove 510 is formed is preferably from 0.01 to 0.8, more preferably from 0.01 to 0.5, most preferably from 0.03 to 0.5.

The depth D of each antileakage groove 510 is preferably from 0.3 mm to 8 mm, more preferably from 0.3 mm to 3 mm, further preferred range being 0.5 mm to 2 mm.

If the width w of each antileakage groove 510 is smaller than 0.1 mm, suppression of the spread of the body fluids which flow on the upper surface of the topsheet 502 or ooze through the interior of the topsheet 502 via the antileakage groove 510 is occasionally lessened. In contrast, if the width w is larger than 20 mm, the feeling during wear is sometimes bad.

If the ratio of the depth D of each antileakage groove 510 with respect to the thickness TO of the portion of the sanitary napkin where no antileakage groove 510 is formed is smaller than 0.01, the antileakage groove 510 is too shallow to effectively trap the body fluids which flow on the upper surface or ooze through the interior. In contrast, if the ratio is larger than 0.8, since the groove portion is compressed hard to overly increase the rigidity of the antileakage groove 510, sometimes the feeling during wear is bad. Therefore, the above range is preferred.

If the depth D of each antileakage groove 10 is smaller than 0.3 mm, the groove 10 is too shallow to effectively suppress the spread of body fluids. In contrast, if the depth D is larger than 8 mm, feeling during wear is bad. Therefore, the above range is preferred.

The width Wa of each hydrophobic area A" is preferably from 3 mm to 30 mm, and the width Wb of the absorption area B" located between the pair of hydrophobic areas A" is preferably from 30 mm to 70 mm. If the width Wa of each hydrophobic area A" is smaller than 3 mm, the width of the hydrophobic area is too narrow to smoothly form the groove in the hydrophobic area A". In contrast, if the width Wa is larger than 30 mm, the width of the absorption area B" becomes too narrow and the absorptive ability is sometimes degraded. Therefore, the above range is preferred. If the width Wb of the absorption area B" is smaller than 30 mm, the absorption area becomes too narrow to consistently absorb the body fluids during various wearing conditions. In contrast, if the width Wb is larger than 70 mm, the provision of the hydrophobic areas requires the width of the absorbent article to increase beyond that which is comfortable to wear.

The distance d1 from the inner side edge of each hydrophobic area A" to each antileakage groove 510 is preferably from 1 mm to 20 mm, and the distance d2 from the outer side edge (side edge of the sanitary napkin) of each hydrophobic area A" to each antileakage groove 510 is preferably from 1 mm to 20 mm. If the distance d1 is smaller than 1 mm, the hydrophobic area becomes too narrow and the amount of body fluids which spread from the antileakage groove 510 is increased, to thereby occasionally create leakage. In contrast, if the distance d1 is larger than 20 mm, the hydrophobic area becomes too large, reducing the dimension of the absorption area B". Therefore, the above range is preferred. If the distance d2 is smaller than 1 mm, the distance from the antileakage grooves 510 to the longitudinal side edges of the absorbent article becomes too small, and the lower layer sometimes contacts the antileakage grooves 510 depending on wearing conditions, thus causing side leakage. In contrast, if the distance d2 is larger than 20 mm, the hydrophobic areas A" disposed outwardly of the antileakage grooves 510 sometimes cover the antileakage grooves during wearing of the absorbent article.

In addition to the effects exhibited by the sanitary napkin of the first embodiment, since the antileakage grooves 510 of the sanitary napkin 501 according to the sixth embodiment include the hole portions 511 communicating with the interior of the absorbent member 504, the body fluids, which flow on the surface material (topsheet 502), can temporarily be stored in the antileakage grooves 510 and then introduced into the absorbent member 504 from the hole portions 511. This arrangement excels in preventing side leakage since any surface flow oozing through the interior of the topsheet, etc. which can cause side leakage is very efficiently suppressed.

Further, as discussed, due to the provision of the pair of hydrophobic areas A", body fluids do not ooze out and body fluids which flow on the upper surface are also absorbed into the absorbent member 504 through the hole portions 511 in the antileakage grooves 510, thus effectively prevent the occurrence of side leakage.

The seventh embodiment of a sanitary napkin serving as an absorbent article of the present invention will now be described with reference to FIG. 9.

Figure 9:
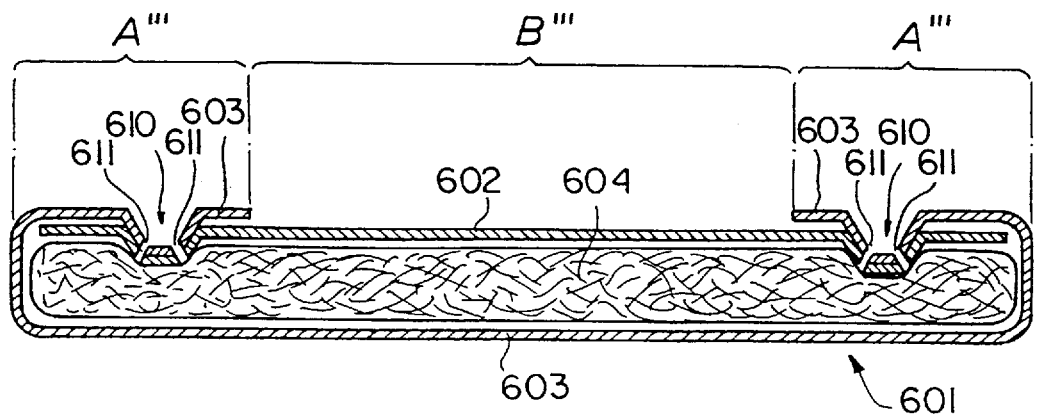
FIG. 9 is a width-wise sectional view showing the seventh embodiment of a sanitary napkin serving as the absorbent article of the present invention.

In the sanitary napkin 601 according to the seventh embodiment shown in FIG. 9, the topsheet 602 is provided only on the upper surface of the absorbent member 604, and the backsheet 603 serving as an antileakage sheet covers the area from the lower surface of the absorbent member 604 to the longitudinal side edge portions of the topsheet 602. Due to this arrangement, a pair of hydrophobic areas A''' are formed at longitudinal side portions of the upper surface of the sanitary napkin, and an absorption area B''' is formed between those hydrophobic areas A'''.

The absorbent article of the present invention should, by no means, be limited to the above sixth and seventh embodiments, and various modifications can be made without departing from the spirit and scope of the present invention.

For example, in the above sixth and seventh embodiments, discontinuous antileakage grooves are provided. However, the grooves may be formed as a single continuous antileakage groove. The discontinuous antileakage grooves are not limited in configuration (configuration of a plan view) to the above embodiments and can take any configurations, e.g., rectangular, circular and the like. The configuration may also take an elliptical shape obtained by rounding the corners of a parallelogram as shown in FIG. 7. The number of the antileakage grooves is not particularly limited, either, and two or more antileakage grooves may be formed at longitudinal side portions, respectively.

Figure 10A:
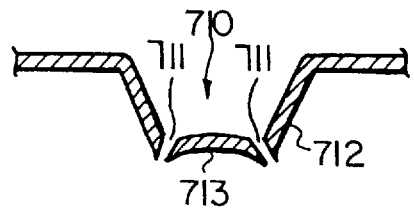
FIG. 10a through FIG. 10d are enlarged width-wise sectional views of an absorbent article showing another example of an antileakage groove in the sixth and seventh embodiments.
Figure 10B:
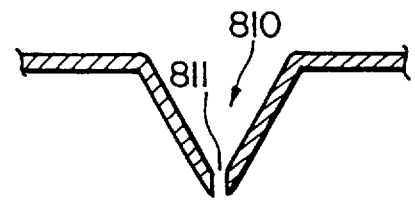
Figure 10C:
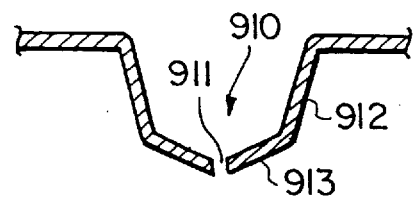
Figure 10D:
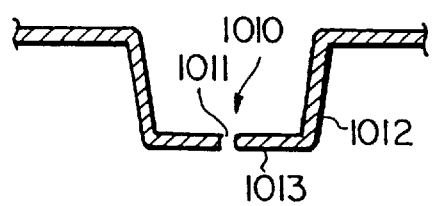

In the embodiment of FIGS. 7 and 8, the sectional configuration of each antileakage groove 510 is square, but it can take any other suitable configuration, such as one in which the bottom surface portion 713 of the antileakage groove 710 exhibits an uneven shape as shown in FIG. 10*a*, one in which the cross section exhibits a triangular shape as shown in FIG. 10*b*, and one in which the bottom surface portion 913 of the antileakage groove 910 is further depressed downwardly. The hole portions 811, 911, 1011 may be located at the central portion in the width direction of each antileakage groove 810, 910, 1010 as shown in FIGS. 10*b* through 10*d*.

The form of the absorbent article is not limited either. In interesting alternatives there is no provision of the antileakage groove 10 and the backsheet is rolled up towards the upper surface side of the absorbent article, or longitudinal side edges of the backsheet extend outwardly to provide a pair of flaps.

Next, a method for preparing an absorbent article according to the present invention will be described with reference to FIG. 11.

Figure 11:
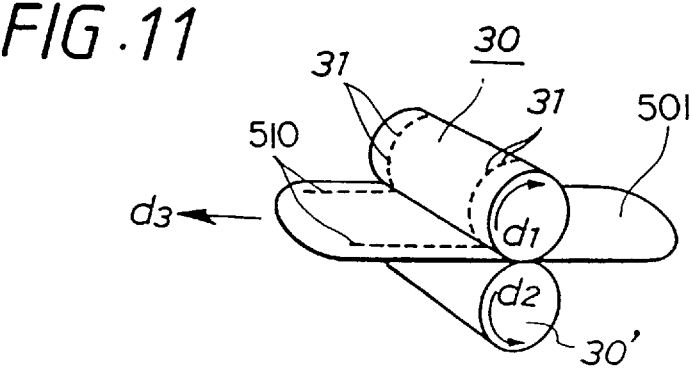
FIG. 11 is a schematic perspective view showing a main part of a method for preparing an absorbent article of the present invention.

Here, FIG. 11 is a schematic perspective view showing a main part of the preparing method according to the present invention.

In the following descriptions, the method is explained by referring to the sanitary napkin according to the sixth embodiment, i.e., the sanitary napkin having the above-mentioned hole portion. However, the method is not restricted thereto but applicable to the sanitary napkins having no hole portion, i.e., the sanitary napkins according to the first to fifth embodiments.

The method for preparing an absorbent article according to the present invention, as shown in FIG. 11, comprises feeding a precursor 501 of an absorbent article having a topsheet, a backsheet and an absorbent member and having hydrophobic areas through an emboss roller 30 thereby forming an antileakage groove 510 along the longitudinal direction of the absorbent article.

More specifically, the absorbent article precursor 501 is fed between the emboss roller 30 having a plurality of projections 31 arranged on opposing longitudinal sides thereof and a presser roller 30' located below the emboss roller 30 in such a manner as to be capable of applying a predetermined amount of pressure to the absorbent article precursor 501 (hereinafter referred to as emboss processing).

Then, through emboss processing, the antileakage grooves 510 are formed by the shearing force of the projections 31 applied to the absorbent article precursor 501, and the hole portion 511 is formed in the area of connection between the bottom surface portion 513 and the peripheral wall portion 512 of each antileakage groove 510.

One preferred example of the emboss roller usable in this embodiment includes a metal roller made of metal such as iron, stainless steel or alloy, and the like. One preferred example of the presser roller includes a metal roller or a rubber roller such as silicone or urethane or the like or a cotton roller and the like.

The emboss processing is preferably performed by means of heat embossing, namely, by heating the emboss roller. By means of heat embossing, the hole portions 511 can be formed while integrally forming the topsheet 502, the antileakage sheet 505 and the absorbent member 504, permitting smoother introduction into the absorbent member 504 of body fluids from the antileakage grooves 510.

The conditions for heat embossing are preferably as follows.

The temperature of the emboss roller 30 is preferably from 100° C. to 180° C., and the pressure to be applied to the absorbent article precursor 501 by the emboss roller 30 and the presser roller 30' is preferably from 0.5 kgf to 50 kgf.

The size and arrangement pitch of the projections 31 can be selected depending on a desired size and arrangement pitch of the antileakage grooves 510.

The absorbent article precursor 501 can easily be prepared by overlapping and adhering the topsheet 502, the backsheet 503, the absorbent member 504 and the antileakage sheet 505, as shown in FIGS. 7 and 8, by a commonly known method.

A sanitary napkin according to the eighth and ninth embodiments will now be described as modified embodiments of the sanitary napkin according to the sixth embodiment with reference to FIGS. 12 and 13.

Only the features different from those of the sanitary napkin of the sixth embodiment will be particularly described. For the features which are not particularly referred to, the descriptions made with respect to the sanitary napkin according to the sixth embodiment are applicable, where appropriate. Members which are identical to those of the first embodiment are denoted by identical reference numerals.

Figure 12:
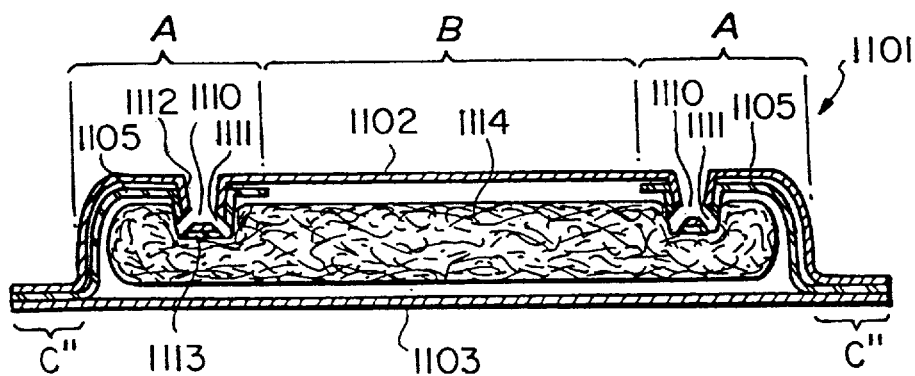
FIG. 12 is a width-wise sectional view (corresponding to FIG. 8) showing the eighth embodiment of a sanitary napkin serving as the absorbent article of the present invention.

In the sanitary napkin 1101 according to the eighth embodiment of FIG. 12, the topsheet 1102 covers the upper surface and longitudinal side surfaces of the absorbent member 1114 and extends outwardly from the side edges of the absorbent member 1114 at the lower surface side of the sanitary napkin 1101. Such extended portions are adhered to the backsheet 1103 with the antileakage sheet 1105 serving as an antileakage sheet interposed therebetween, thereby forming the side flaps C". The antileakage sheet 1105 is provided at each longitudinal side portion of the upper surface of the sanitary napkin 1101 between the absorbent member 1114 and the topsheet 1102. In each antileakage groove 1110, the hole portion 1111 is formed in the area of connection between the bottom surface portion 1113 and the peripheral wall portion 1112, so that body fluids can be introduced into the absorbent member 1114 through the hole portion 1111.

Figure 13:
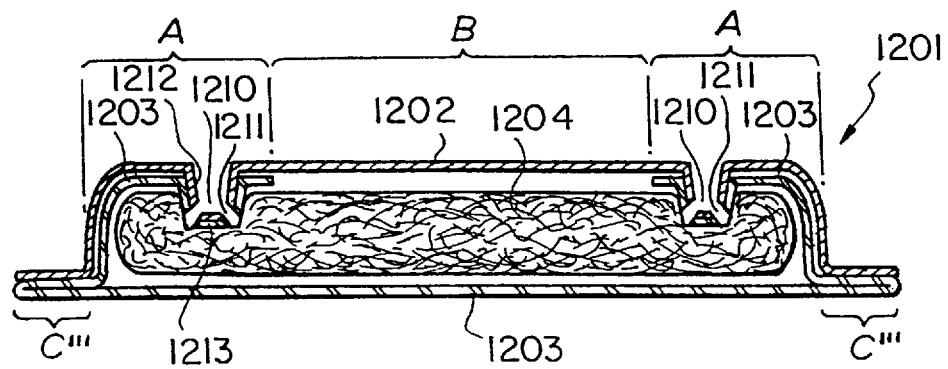
FIG. 13 is a width-wise sectional view (corresponding to FIG. 8) showing the ninth embodiment of a sanitary napkin serving as the absorbent article of the present invention.

In the sanitary napkin 1201 according to the ninth embodiment of FIG. 13, the backsheet 1203 serving as an antileakage sheet extends outwardly from the side edges of the absorbent member 1204 at the lower surface side of the sanitary napkin 1201 and then is bent towards the absorbent member 1204 to cover the side surfaces and the side portions of the upper surface of the absorbent member 1204. The topsheet 1202 covers the upper surface and the longitudinal side surfaces of the absorbent member 1204 and extends outwardly from the side edges of the absorbent member 1204 at the lower surface side of the sanitary napkin 1201. Such extended portions are adhered to the bent backsheet 1203 to form the side flaps C'".

In each antileakage groove 1210, the hole portion 1211 is formed in the area of connection between the bottom surface portion 1213 and the peripheral wall portion 1212, so that body fluids can be introduced into the absorbent member 1204 through the hole portion 1211.

What is claimed is:

1. A substantially elongated absorbent article having a liquid permeable topsheet, a liquid impermeable backsheet, and an absorbent member interposed between said topsheet and said backsheet, said absorbent article further comprising:

a pair of hydrophobic areas along opposing longitudinal side portions of an upper surface of said absorbent article inwardly from longitudinal side edges of said absorbent article, said hydrophobic areas each having a continuous or discontinuous antileakage groove formed along a respective one of the longitudinal side portions, wherein a width of each of said antileakage grooves is from 0.1 mm to 20 mm, a ratio of a depth of each of said antileakage grooves with respect to a thickness of a portion of said absorbent article where no antileakage groove is formed is from 0.01 to 0.8, and the depth of each of said antileakage grooves is from 0.1 mm to 12 mm.

2. The absorbent article according to claim 1, wherein each of said antileakage grooves has at least one hole portion so that body fluids can be introduced into said absorbent member through said at least one hole portion.

3. A method for preparing an absorbent article as defined in claim 1 or 2, which comprises;

feeding a substantially elongated absorbent article precursor comprising a topsheet, a backsheet, an absorbent member interposed between said topsheet and said backsheet and a pair of hydrophobic areas along opposing longitudinal side portions of an upper surface of said absorbent article precursor through an emboss roller thereby forming an antileakage groove in a longitudinal direction of said hydrophobic areas to produce said absorbent article.

4. The method according to claim 3, wherein said feeding step uses an emboss roller which is heated.

5. The method according to claim 3, wherein said emboss roller has a plurality of projections arranged on opposing longitudinal sides of said emboss roller.

6. The absorbent article according to claim 5, wherein the depth of each of said antileakage grooves is from 0.3 mm to 8 mm.

7. The absorbent article according to claim 2, wherein each of said antileakage grooves comprises a bottom portion and a peripheral wall portion, and said at least one hole portion is formed in an area between the bottom portion and the peripheral wall portion.

8. The absorbent article according to claim 1, wherein said hydrophobic areas are formed by providing antileakage sheets comprising said liquid impermeable backsheet or an antileakage sheet other than said liquid impermeable backsheet.

9. The absorbent article according to claim 1, wherein the width of each of the antileakage grooves is from 0.1 mm to 10 mm, the ratio of the depth of each of said antileakage grooves with respect to the thickness of a portion of said absorbent article where no antileakage groove is formed is from 0.3 to 0.8, and the depth of each of said antileakage grooves is from 1 mm to 8 mm.

10. The absorbent article according to claim 1, wherein the width of each of said antileakage grooves is from 0.1 mm to 10 mm, the ratio of the depth of each of said antileakage grooves with respect to the thickness of a portion of said absorbent article where no antileakage groove is formed is from 0.01 to 0.5, and the depth of each of said antileakage grooves is from 0.1 mm to 8 mm.

11. The absorbent article according to claim 1, wherein the width of each of said hydrophobic areas is from 3 mm to 30 mm, and a width of an absorption area located between the pair of hydrophobic areas is from 30 mm to 70 mm.

12. The absorbent article according to claim 1, wherein a distance from an inner edge of each hydrophobic area to each respective antileakage groove is from 1 mm to 20 mm and the distance from an outer longitudinal side edge of each hydrophobic area to each respective antileakage groove is 1 mm to 20 mm.

13. The absorbent article according to claim 1, further comprising a pair of flaps which are formed by extending said backsheet outwardly.

14. The absorbent article according to claim 1, wherein said topsheet covers an upper surface and longitudinal side surfaces of said absorbent member and extends outwardly from side edges of said absorbent member at a lower surface of the absorbent article to form extended portions, said extended portions adhered to extended portions of said backsheet through antileakage sheets disposed along said longitudinal side portions of the upper surface of said absorbent article, said topsheet, antileakage sheets and backsheet forming side flaps.

15. The absorbent article according to claim 1, wherein said antileakage grooves each comprise a bottom surface portion, a peripheral wall portion, and a hole portion between the bottom surface portion and the peripheral wall portion.

16. The absorbent article according to claim 15, wherein an area of said hole portion is from 0.1 mm$^2$ to 20 mm$^2$.

* * * * *